United States Patent [19]

Dempsey et al.

[11] Patent Number: 5,687,734

[45] Date of Patent: Nov. 18, 1997

[54] FLEXIBLE PATIENT MONITORING SYSTEM FEATURING A MULTIPORT TRANSMITTER

[75] Inventors: Michael K. Dempsey, Acton; Mark S. Kotfila, Chelmsford; Robert J. Snyder, Westford, all of Mass.

[73] Assignee: Hewlett-Packard Company, Palo Alto, Calif.

[21] Appl. No.: 326,614

[22] Filed: Oct. 20, 1994

[51] Int. Cl.$^6$ ............................................. A61B 5/0402
[52] U.S. Cl. ................................... 128/696; 128/903
[58] Field of Search .............................. 128/630, 637, 128/639, 653.1, 668, 670, 687, 690, 695, 696, 700, 709, 716, 897, 903, 904, 906; 607/5; 364/443.02, 443.03, 443.04, 443.06

[56] References Cited

U.S. PATENT DOCUMENTS

| | | |
|---|---|---|
| 3,946,159 | 3/1976 | Fay . |
| 3,986,498 | 10/1976 | Lewis . |
| 4,150,284 | 4/1979 | Trenkler et al. ............ 364/413.06 |
| 4,715,385 | 12/1987 | Cudahy et al. . |
| 4,952,928 | 8/1990 | Carroll et al. . |
| 5,012,411 | 4/1991 | Policastro et al. ............ 364/413.06 |
| 5,022,404 | 6/1991 | Hafner . |
| 5,025,808 | 6/1991 | Hafner . |
| 5,062,151 | 10/1991 | Shipley . |
| 5,086,776 | 2/1992 | Fowler, Jr. et al. . |
| 5,086,778 | 2/1992 | Mueller et al. ............ 364/413.06 |
| 5,113,869 | 5/1992 | Nappholz et al. .............. 128/903 |
| 5,238,001 | 8/1993 | Gallant et al. . |
| 5,257,627 | 11/1993 | Rapoport ........................ 128/904 |
| 5,307,263 | 4/1994 | Brown ........................ 364/413.02 |
| 5,319,355 | 6/1994 | Russek . |
| 5,319,363 | 6/1994 | Welch et al. . |
| 5,331,549 | 7/1994 | Crawford, Jr. .............. 364/413.03 |
| 5,338,157 | 8/1994 | Blomquist . |
| 5,339,822 | 8/1994 | Taylor et al. . |
| 5,351,694 | 10/1994 | Davis et al. . |
| 5,375,604 | 12/1994 | Kelly et al. . |
| 5,417,222 | 5/1995 | Dempsey et al. . |
| 5,431,171 | 7/1995 | Harrison et al. . |
| 5,441,047 | 8/1995 | David et al. ................... 128/904 |
| 5,458,123 | 10/1995 | Unger . |

FOREIGN PATENT DOCUMENTS

| | | |
|---|---|---|
| 472 411 A1 | 2/1992 | European Pat. Off. . |
| 0553372A1 | 8/1993 | European Pat. Off. . |
| 0601589A2 | 6/1994 | European Pat. Off. . |
| 0601589A3 | 6/1994 | European Pat. Off. . |
| 405095914 | 4/1993 | Japan ........................ 128/904 |
| 83/03744 | 11/1983 | WIPO . |
| WO94/14128 | 6/1994 | WIPO . |

*Primary Examiner*—William E. Kamm
*Attorney, Agent, or Firm*—Mark Z. Dudley

[57] ABSTRACT

A flexible patient monitoring system which interfaces a telemetry subsystem with a network by way of a telemetry transmission receiving system and a network controller. The telemetry subsystem includes one or more monitoring instruments, a multiport transmitter, a telemetry subsystem interface, a backchannel receiver module, and a telemetry docking station. The flexible patient monitoring system may be configured to operate in at least four modes: ambulatory telemetry mode, wherein the multiport transmitter is operated independently of other monitoring instruments and is powered by an internal power source; docked telemetry mode, wherein the multiport transmitter is connected to the telemetry docking station for transfer of data and power; simple instrument telemetry mode, wherein the multiport transmitter and a primary monitoring instrument or an auxiliary monitoring instrument are connected together for transfer of data; and docked instrument telemetry mode, wherein the multiport transmitter and a primary monitoring instrument or an auxiliary monitoring instrument are attached to the telemetry docking station for transfer of data (and optionally for transfer of power to the multiport transmitter). Wireless communications between the telemetry subsystem and various nodes on the network are thus enabled. Information may be provided to and from the telemetry subsystem interface via the multiport transmitter.

17 Claims, 5 Drawing Sheets

FLEXIBLE PATIENT MONITORING SYSTEM FEATURING A MULTIPORT TRANSMITTER

TECHNICAL FIELD OF THE INVENTION

This invention relates to patient monitoring systems and more particularly to an ambulatory patient monitoring system that is reconfigurable to facilitate the collection and use of monitored information, particularly in a hospital or other institutional setting.

BACKGROUND OF THE INVENTION

Hospitals and other medical care institutions provide differing levels of patient care so as to conserve resources, minimize the costs of patient care, and maximize patient outcomes (i.e., the condition or health of the patient). To achieve this, the attending staff will transfer a patient between different units in the hospital in accordance with the acuity of the patient's condition. For example, a high-acuity patient may be admitted to an intensive care unit (ICU) or critical care unit (CCU), then is transferred to an intermediate care unit, and so on to successively less-intensive care environments until the patient is released from the hospital. Such a paradigm of transitional medical care has been precipitated by the increasing costs of providing medical care, and the increasing acuity of the patients that receive such medical care. For example, the average acuity of the patients that are transferred to an intermediate care environment is now higher than in the past. More particularly, a patient that is transferred to an intermediate care unit is now likely to require a more intensive level of continuing care in comparison to the level of care required by such a patient in years past.

For the attending staff to successfully practice such medical care, the patient monitoring applied to each patient must be easily reconfigured according to the patient's condition, acuity, and location. However, the conventional patient monitoring system for a non-ambulatory patient typically employs a fixed, dedicated bedside monitor that is located and dedicated for use in a bedside-monitored environment. The bedside monitor is usually wall-mounted, configured for use at one bed, and hardwired to a particular hospital communications network. Such instruments are expensive, and thus typically are in short supply, and they are not easily reconfigured when the patient transfers between beds, rooms, or environments.

An ambulatory patient may be assigned a telemetry transmitter that is worn by the patient such that telemetry data is transmitted to an array of telemetry antennas and receivers, which are connected to the hospital communications network. Reconfiguring the patient monitoring system at transitions between non-ambulatory and ambulatory monitoring modes is a difficult, expensive, and time-consuming task, and typically results in a gap or discontinuity in the stream of monitor data. As a result, a conventional monitoring system is not well-suited for use in a transitional care practice.

In particular, the conventional telemetry transmitter is designed to be worn by the patient so that the patient is free to move within a selected area of the hospital while still being monitored. The telemetry transmitter is made as simple, compact, and light in weight as possible. The telemetry transmitter typically lacks either a display for viewing representations of the monitored outputs or a data input device for manual entry of data. The telemetry transmitter is designed to operate independently of other monitoring instruments and offers no direct connection or interface between a monitoring instrument and the hard-wired network.

The conventional telemetry transmitter relies solely on an internal battery for power, and as such the unit must be designed and operated to minimize battery usage. For these reasons, and also to reduce cost, the telemetry transmitter contains only a minimum of physiological monitoring devices (typically, only an electrocardiogram or ECG), a simple processor device that is programmed only to process information received from the monitoring devices and convert it into suitable form for wireless transmission, and a low-power radio frequency (RF) transmitter for outputting the processed monitor information.

The foregoing may thus be seen to limit the versatility and usability of the telemetry transmitter, especially in situations where the telemetry transmitter is the only monitoring device applied to the patient. Such situations include:

(a) When the telemetry transmitter is being placed on the patient, and an attendant must assure that the physiological sensors are properly mounted to provide the desired signal.

(b) When hospital staff need to monitor routine physiological information while present in the patient's room, such as when vasoactive drugs are administered to the patient.

(c) During installation, reconfiguration, repair, or troubleshooting of the telemetry transmitter or other components of the network.

(d) When the patient's acuity escalates, which in some instances may be to a critical or life-threatening state, and the level of patient monitoring must be scaled up. Often, the requisite equipment (such as a defibrillator) is not proximate the patient, and yet it must be applied rapidly to the patient before the clinician can diagnose the problem and act to alleviate the problem.

(e) When a plurality of physiologic parameters must be monitored, and the telemetry transmitter is not equipped to measure all of the parameters. Typically, the additional parameter(s), such as non-invasive blood pressure (NIBP), can only be monitored by attaching other full-featured instruments (such as a bedside monitor).

(f) When there is a need to send information from the patient's bedside to the central station, either for viewing by personnel at that station or for storage with the patient's records. Such a capability would speed the flow of data into the system and improve patient care and reduce errors. In the typical approach, such information is transcribed or downloaded from a recorder carried attending staff, or by manual data entry of handwritten notes.

Further, while it may be desirable to implement more capabilities in a patient monitoring system so as to resolve such drawbacks, it is also desirable that such capabilities be achieved without any significant increase in the telemetry transmitter's cost, size, weight, and power usage.

Accordingly, there is a need for a flexible patient monitoring system, which for the purposes of this application is defined as a monitoring system that: is reconfigurable, preferably by the attending staff, with minimal difficulty and disruption; accomplishes continuous monitoring of a patient even while the monitoring system is reconfigured; offers the ability to rescale the level of monitoring in accordance with changes in the patient's acuity and care environment; and offers the option of operating in either wireless or hard-wired telemetry modes.

SUMMARY OF THE INVENTION

Accordingly, a preferred embodiment of a flexible patient monitoring system may be constructed for use in monitoring a selected plurality of physiological conditions of a patient in a medical care environment. The flexible monitoring system includes a multiport transmitter having a sensor system connectable to the patient for providing sense signals representative of the selected plurality of physiological conditions; a monitoring section for receiving the sense signal and providing first data representative of the selected plurality of physiological conditions; a first data port for receiving externally-sourced data; and a data processing and signal transmission section for processing the first data and the externally-sourced data so as to provide processed data, and for transmitting the processed data as a telemetry signal.

In a second preferred embodiment, the flexible patient monitoring system further includes a monitoring instrument for providing the externally-sourced data. The multiport transmitter is connectable to the monitoring instrument for receiving the externally-sourced data, processing the first data and the externally-sourced data, and transmitting the processed data as a telemetry signal.

In a third preferred embodiment, the flexible patient monitoring system further includes a telemetry subsystem interface, and the multiport transmitter is connectable to the telemetry subsystem interface for transferring data therebetween. Such transferred data may include the externally-sourced data.

As will be described in more detail in the following description, the flexible patient monitoring system resolves a number of deficiencies found in prior art systems. For example, when it is determined that the patient is experiencing a medical emergency, readings taken by the multiport transmitter can trigger an alarm at the telemetry subsystem interface and at a network node such that the patient's condition can be viewed and utilized immediately by attending staff located both in the bedside environment and at a network node.

When the patient's acuity increases, or otherwise indicates the need for additional monitoring instruments, such instruments may be rapidly connected to the multiport transmitter for more extensive monitoring. Thus, there need be no delay that otherwise would occur in attaching the additional monitoring instrument directly to the patient before remedial procedures are initiated. When the patient's acuity decreases, the attending staff may easily reconfigure the patient monitoring from given level of monitoring to a less-extensive level of monitoring, such as in a reconfiguration from bedside monitoring to ambulatory monitoring.

With use of the flexible patient monitoring system taught herein, a hospital can maintain a less-extensive array of bedside connections to the network. Fewer racks of expensive monitoring equipment need be distributed about the hospital for emergencies, and the medical personnel that respond to an emergency are better informed as to which emergency equipment is needed.

Routine procedures also benefit from the readout capability offered by the telemetry subsystem interface, thus simplifying the charting of the patient, and the diagnosis, monitoring, and treatment of the patient by attending staff and other medical personnel at the patient's bedside. Further, the contemplated patient monitoring system allows attending staff, when charting a patient, to be able to transmit readings and observations to a network node. This procedure allows recordation of readings as they are being taken, rather than by storing such information on a charting device or as handwritten notes.

The many advantages described herein are achieved without making the multiport transmitter substantially greater in size, weight, battery use, or cost in comparison to the conventional telemetry transmitter.

The foregoing and additional advantages of the invention will be apparent from the following detailed description of preferred embodiments of the invention, as illustrated in the accompanying drawings.

DETAILED DESCRIPTION OF THE INVENTION

Flexible Patient Monitoring System

Figure 1:
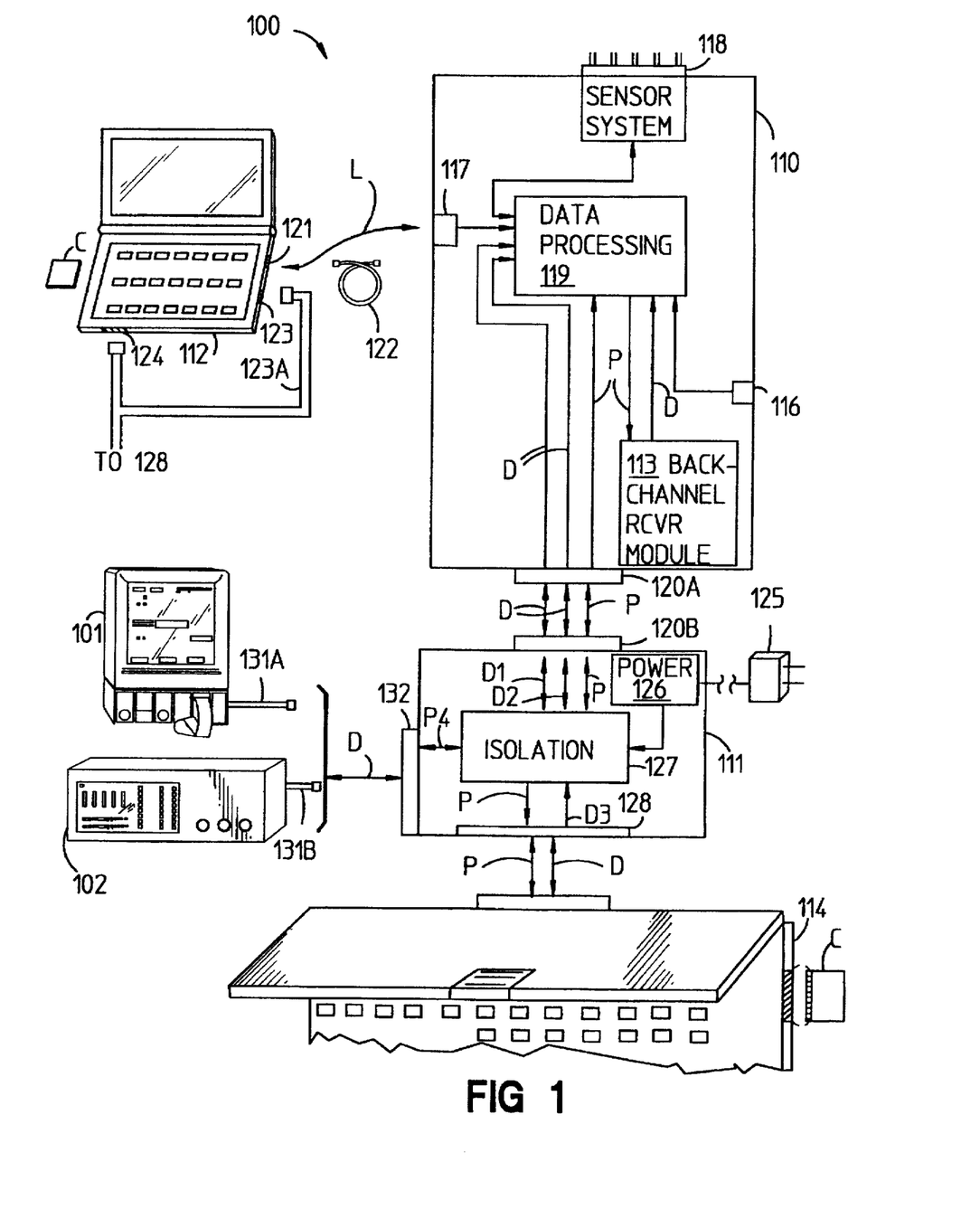
FIGS. 1 and 2 are simplified representations of a flexible patient monitoring system constructed in accordance with the present invention.
Figure 2:
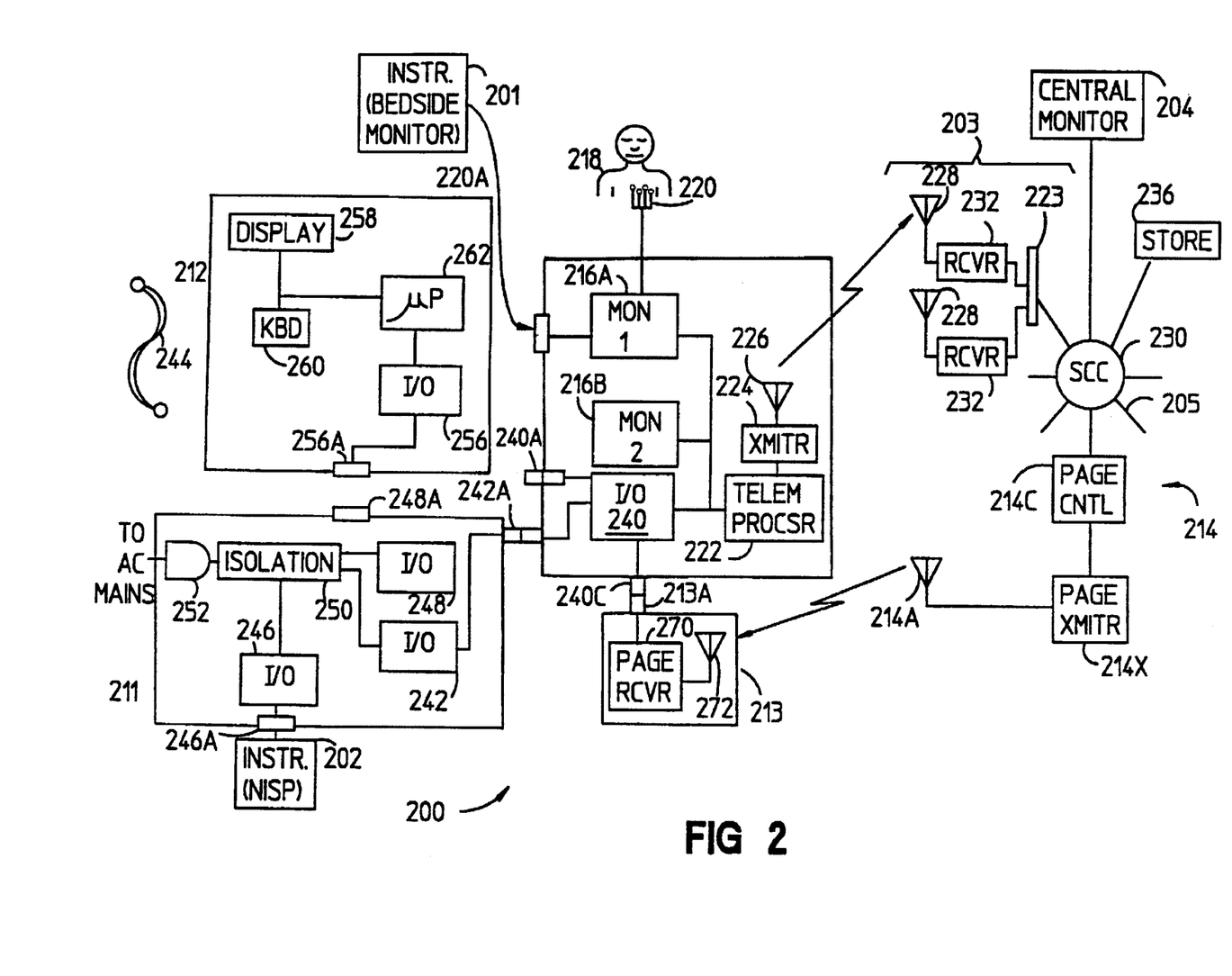

The present invention provides increased flexibility in an improved patient monitoring system without requiring significant increase in the size, weight, cost, or battery usage of a telemetry transmitter. As will be understood with reference to FIGS. 1 and 2, a telemetry subsystem 100 and a flexible patient monitoring system 200 may be constructed according to the present invention. The telemetry subsystem 100 include certain ones of the following components, depending upon the mode of patient monitoring to be performed, and the particular environment(s) in which the subsystem is operating:

a primary monitoring instrument 101 an auxiliary monitoring instrument 102 a multiport transmitter (MPX) 110 a telemetry docking station 111 a telemetry subsystem interface, e.g., a portable processor 112 or portable computer 114 a backchannel receiver module 113

The flexible patient monitoring system 200 includes the telemetry subsystem 100 and one or more of the following components:

a system communications network 205, which includes nodes such as a central monitoring station 204 a telemetry signal receiving system 203 a backchannel transmission system 214

The primary monitoring instrument 101 and/or the auxiliary monitoring instrument 102 preferably are instruments equipped to perform data management and recording functions, and to monitor one or more of the following physiological parameters:

electrocardiogram/respiration (ECG/RESP)

electrocardiogram (ECG)

invasive pressures temperature non-invasive blood pressure (NIBP)

$SpO_2$/Pleth level carbon dioxide level ($CO_2$)

cardiac output

TcGas

A first preferred embodiment of the multiport transmitter (hereinafter, MPX) 110 may be operated to independently monitor a selected plurality of physiological parameters, preferably selected from the above-listed set physiological parameters, and to transmit data representative of the selected parameters in a telemetry signal to the system communications network 205. The first preferred embodiment of the MPX 110 may also be concurrently operated to receive externally-sourced data, such as may be originated at the primary monitoring instrument 101, auxiliary monitoring instrument 102, portable processor 112, and/or portable computer 114, and to process the received data for subsequent transmission in the telemetry signal to the system communications network 205. The MPX 110 includes a call signal activator preferably in the form of a nurse call button 116, an optical data transceiver preferably in the form of a serial infrared (SIR) port 117, a sensor system 118, a data processing and signal transmission section 119, and a power and data port 120.

A first preferred embodiment of the backchannel receiver module 113 may be incorporated within the MPX 110 (as shown in FIG. 1) or, in a second preferred embodiment, may be constructed as a detachable backchannel receiver module 213 (as shown in FIG. 2). In a particularly preferred embodiment, the backchannel receiver module 113, 213 is operable for receiving and translating signals transmitted on a paging radio-frequency communication band from the backchannel transmission system 214. Such backchannel transmission system 214 includes a backchannel controller 214C, backchannel transmitter 214X, and antenna 214A.

The telemetry subsystem interface is preferably provided in the form of a portable processor 112, or a portable computer 114. A preferred embodiment of the portable processor 112 is a Hewlett-Packard 200LX palmtop processor. The portable computer 114 is preferably provided in the form of a notebook computer. A preferred embodiment of the portable computer 114 is a Hewlett-Packard Omnibook superportable computer.

Application software resident on the portable processor 112 or portable computer 114 provides control and interfacing functions with respect to the MPX 110 transmitter. Software for operating the portable processor 112 or the portable computer 114 may be installed via a plug-in memory module, preferably in the form of a memory card C (such as a PCMCIA card). For example, the portable processor 112 can initiate communication with the MPX 110 transmitter automatically upon program execution and establishment of a communication link for transfer of control and data signals. The contemplated communications link may be effected through a first data port, preferably in the form of an optical communications transceiver 121 via light beam L, or via an optical fiber cable 122. Alternatively, a communications link may be effected at a second data port preferably in the form of a serial data interface 123 coupled to a data portion of a multiconductor data and power cable 123A. Power may be transferred to the portable processor 112 via a power cable portion of the multiconductor data and power cable 123A to a DC input jack 124.

A first preferred embodiment of the telemetry docking station 111 includes a first data and power port 120B for connecting power lines P and data paths D1, D2 between the telemetry docking station 111 and the MPX 110. Power may be supplied to the telemetry docking station 111 from a permanent power source (e.g., an AC outlet) via an AC/DC converter 125 through a power conditioning circuit 126 and an isolation circuit 127. Additional power lines P and a data path D3 are connected to the portable processor 112 or portable computer 114 via a second data and power port 128. An additional data path D4 is connected to the primary monitoring instrument 101 or auxiliary monitoring instrument 102 via a first data port 132 to which a monitoring instrument multiconductor cable 131A or 131B may be connected. The data transferred via the multiconductor cables 123A, 131A, 131B is preferably formatted according to a standard serial data interface protocol, such as the Hewlett-Packard MECIF Interface Standard.

The isolation circuit 127 provides isolated, conditioned power to the MPX 110, portable processor 112, and portable computer 114, thus providing reliable, isolated power and relieving those units from the need to operate on other power sources, such as internal batteries. The isolation circuit 127 also provides electrically-isolated transfer of data between the MPX 110, portable processor 112 or portable computer 114, the primary monitoring instrument 101, and the auxiliary monitoring instrument 102. For portability, the telemetry docking station 111 is preferably provided in a compact, light, low-profile form factor similar to that of the portable processor 112 (e.g., of dimensions less than or comparable to that of the interior of a coat pocket, at approximately 16×9×3 centimeters).

As particularly illustrated in FIG. 2, a second preferred embodiment of the MPX 210 contains first and second physiological monitoring sections 216A, 216B which are respectively provided in the form of an ECG monitor and an $SpO_2$ monitor. (The use of additional or substitute monitoring sections are contemplated as being within the teachings of the present invention, such as a non-invasive blood pressure parameter (NIBP) monitor, a brainwave monitor, and/or other suitable physiological monitors, depending on the need.) The first physiological monitoring section 216A may be connected to the patient 218 by a sensor 220. For example, for ECG monitoring, the sensor 220 would be connected to electrodes attached to the patient's chest. As will be described below, a certain ones of the conductors in sensor 220 may also be employed as a data communications link 220A to a primary monitoring instrument 201.

Sense signals derived by the monitoring sections 216A, 216B are fed to a telemetry processor 222 which preferably includes a suitably-programmed microprocessor for conversion of the sense signals to a suitable telemetry signal for transmission to the central monitoring station 204. The telemetry processor 222 may also contain signal interface circuitry, signal processing circuitry, a power supply section, and memory sections(s) for storage and retrieval of selected information concerning the patient 218 or the operation of the MPX 210. The telemetry processor 222 is also programmed to perform other processing functions, such as error-checking, self-testing, and the like.

A telemetry signal is output from the telemetry processor 222 to a frequency-synthesized transmitter 224 for broadcast at a suitable output element 226. Depending on the telemetry needs in the hospital, the transmitter 224 and output element 226 may be constructed to radiate at a selected frequency in the radio frequency (RF) band; the output element 226 may be integrated into the sensor 220 or may be otherwise situated in the MPX 210. An alternative embodiment of the transmitter 224 and output element 226 may be constructed to radiate at a selected frequency in the optical transmission band, for example, an infrared frequency.

The telemetry signal emitted by the output element 226 is received by one of a plurality of receiving elements 228 and telemetry receivers 232 suitably located in the hospital. Telemetry signals acquired by the plurality of telemetry receivers 232 are applied to a telemetry receiver interface 233 for translation to network telemetry data, which is transferred to a network controller 230 preferably in the form of a serial communications controller (SCC). The network telemetry data is then transferable to other nodes on the network 205 such as the central station 204. Such nodes may be considered local nodes, that is, in locations proximate to the patient 218, and other nodes may be quite remotely situated. The local nodes on the network 205 are contemplated as including suitable data terminals, workstations, and the like so as to make the network telemetry data available to hospital staff at a network node in a clinical or surgical setting, a physician's office, a hospital pharmacy, a diagnostic laboratory, a data processing and record-keeping center, and similar departments or locations within the hospital. Additional password-protected, secure connections to communications networks outside the hospital, such as telephone and radio networks, allow authorized persons to access the network telemetry data at remote nodes (i.e., nodes located outside of the hospital).

The telemetry network data may be processed at any node on the network 205. For instance, the central monitoring station 204 may perform further processing so as to derive patient information and may selectively store such information in temporary or bulk storage devices 236. The central monitoring station 204 and may cause images indicative of such patient information to be selectively displayed on one or more displays. For instance, medical personnel that have access to the central monitoring station 204 may monitor and react to relevant physiological conditions of the patient.

The MPX 210 features an input/output (I/O) section 240 that operates first, second, and third ports 240A, 240B, 240C. The first port 240A may, for example, be a wireless transceiver data port, such as one including an IR transmitter and complying with the serial infrared (SIR) data transmission protocol designed by the Hewlett-Packard Company. Such a first port would interface with one or more SIR receivers present on the portable processor 212 as described above. The second port 240B may be directly connected to the telemetry docking station 211 at a respective port 242A and serve as a power and data communications interface between the MPX 210 and the telemetry docking station 211. The third port 240C may connect to a backchannel receiver module 213 as will be discussed below.

The telemetry docking station 211 includes a first, second, and third I/O sections 242, 246, 248 and respective ports 242A, 246A, 248A. A power isolation section 250 and a power conditioning section 252 are connectable to a permanent power source (not shown) such as the hospital main electrical system. The second I/O section 246 serves as a data interface to an auxiliary monitoring instrument 202. The third I/O section 248 and port 248A serve as a data interface operable with an I/O section 256 and port 256A on the portable processor 212. Preferably, the ports 248A and 256A are provided in the form of infrared transceiver ports.

Reconfiguration of the Flexible Patient Monitoring System

The flexible patient monitoring system 200 may be configured to operate in at least four modes:

1) ambulatory telemetry mode, wherein the MPX 210 is operated independently of other monitoring instruments and is powered by an internal power source;
2) docked telemetry mode, wherein the MPX 210 is connected to a telemetry docking station 211 for transfer of data and power;
3) simple instrument telemetry mode, wherein the MPX 210 and a primary monitoring instrument 201 or an auxiliary monitoring instrument 202 are connected together for transfer of data therebetween, and
4) docked instrument telemetry mode, wherein the MPX 210 and a primary monitoring instrument 201 or an auxiliary monitoring instrument 202 are attached to the telemetry docking station 211 for transfer of data therebetween (and optionally for transfer of power to the MPX 210).

A portable processor 212 may also be optically connected to the MPX 210 in the ambulatory telemetry mode. The portable processor 212 (or the portable computer 114) may also be optionally connected to the telemetry docking station 211 in the docked telemetry mode or the docked instrument telemetry mode for transfer of data and power.

For example, when the MPX 210 is operated in the instrument telemetry mode, an operator can determine at the bedside what primary monitoring data is to be transmitted to the network 205 by use of an instrument telemetry configuration frame displayed on the primary monitoring instrument 201. Data will be transferred from the primary monitoring instrument 201 to the MPX 210, which will receive, multiplex, compress, format, and transmit the data as a telemetry signal to a telemetry signal receiving system 203. Receivers located in the telemetry signal receiving system 203 receive the telemetry signal and the telemetry receiver interface 233 uses appropriate protocols to convert the telemetry signal into network data messages for transmission over the network 205. The flexible telemetry system 200 can thereby transfer patient monitoring data, control signals, alarm signals, and other information from the MPX 210 (or an instrument connected to the MPX 210) to any node on the network, such as the node occupied by a central monitoring station 204.

In particular, the MPX 210 can provide a wireless connection of the portable processor 212, the portable computer 114, the primary monitoring instrument 201, and/or the auxiliary monitoring instrument 202 to the network 205. Further, data received by the MPX 110 from the portable processor 212, the portable computer 114, the primary monitoring instrument 201, and/or the auxiliary monitoring instrument 202 may be monitored at the patient's location, without any need for a hard-wired network connection.

Due to its multiplicity of communication ports, the MPX 210 may be easily reconfigured to and from ambulatory mode, docked telemetry mode, simple instrument telemetry mode, or docked instrument telemetry mode. This flexibility allows the flexible patient monitoring system 200 to be reconfigured while the patient 218 occupies or moves between any of the hospital areas that are serviced by receiving elements 228. This reconfiguration may be accomplished while still permitting continuous monitoring of relevant patient physiological conditions. As a result, the task of patient monitoring is effected more flexibly and inexpensively, patient bed transfer costs are reduced, and the number and acuity of the patients that are monitored is greater than in a conventional patient monitoring system.

Preferably, the telemetry signal contains status information pertaining to the monitoring mode as well as the type of data being transmitted. The telemetry signal receiving system 203 includes data acquisition software modules for determining whether the data received is ambulatory telemetry data or instrument telemetry data, and formatting the received telemetry data into a form appropriate for transmission on the network. For instance, the central monitoring station 204 may receive telemetry data that has been formatted to cause differing user interfaces to be displayed on the central monitoring station, according to whether the data represents information derived from an ambulatory telemetry mode or an instrument telemetry mode. As a further example, recording requests from the primary monitoring instrument 201 may be formatted into the various types of recordings supported by different nodes of the network 205.

In some instances of ambulatory mode operation, it may be advantageous to couple the MPX 210 to the portable processor 212 via IR transceivers in the ports 256A and 240A such that the telemetry docking station 211 need not be used. The two units (MPX 210 and portable processor 212) may be physically coupled as well, to form a single, portable package. When necessary, an optical fiber cable 244 may be connected between suitable terminals on the ports 240A, 248A, or 256A to effect light-tight transmission between I/O sections 240, 248, or 256.

The portable processor 212 includes a data output device preferably in the form of a liquid crystal display or some other type of flat screen display 258, a data input device such as a keyboard 260, and a microprocessor section 262. The I/O section 256 may be operated to communicate information to and from the microprocessor 262. Memory sections included in the microprocessor for storing information allows the microprocessor to be programmed to perform selected processing tasks on the received data. For example, a representation of telemetry data acquired from the MPX 210 may be displayed on display 258 and the nature of this representation may be varied by a user according to commands or queries entered on the data input device 260. The user may select from a variety of a representations, including ECG waveforms, a transmitter frequency chart, trend graphs, or other useful information. While not specifically indicated in FIG. 2, the portable processor 212 is contemplated as incorporating or accommodating other forms of data input devices such as a microphone, roller ball, touch screen, pen-based input panel, or the like. Similarly, the portable processor 212 may incorporate other forms of data output devices, such as an annunciator for sounding an audible signal, or acoustic transducer for reproducing a voice. Components for carrying out the performance of other processing tasks (not shown) may be included in the portable processor 212 as known in the art, such as extended memory cards, facsimile/modem cards, and the like.

Keyboard inputs, either as generated, or as modified by processor 262, may be applied through I/O port 256 to I/O port 242, and from I/O port 240 to the telemetry processor 212. Such inputs may, for example, represent commands to change the mode of ECG monitoring by the monitor sections 216A, 216B between diagnostic and monitoring quality; if the monitor sections 216A, 216B are adapted for monitoring a variety of physiological conditions, the condition being monitored can be changed. The outputs from the monitoring sections 216A, 216B may be processed by the telemetry processor 212 according to commands inputted from keyboard 260. Data entered at keyboard 260 may also be passed through processor 262, I/O sections 256, 248, 242, and 240, and telemetry processor 212 to transmitter 224 for transmission to the central monitoring station 204. Such data may be utilized, for example, to effect diagnostic routines on one or more of the components of the flexible monitoring system 200.

Backchannel Communications

A backchannel receiver module 213 is detachably mounted on the MPX 210, preferably at port 240C. The backchannel receiver module 213 includes a communications and power port 213A, a backchannel receiver 270, and receiving antenna 272. Data originating from any node on the network 205 may be directed to the backchannel communications controller 214C for addressable transmission to a particular backchannel receiver module 213. That is, each message sent by backchannel transmitter 214X would include an encoded address so that it is received and/or utilized only by the backchannel receiver module 213 for which it is intended. Once received and translated, the message is provided to the I/O section 240 of the MPX 210.

The backchannel receiver 270 may operate on an integral battery power source and alternatively may be operated via power provided through the communications and power port 213A; such power may originate from the MPX 210 or from the telemetry docking station 211. The requisite circuitry and components that comprise the backchannel receiver 270 and receiving antenna 272 may be constructed in a package that is extremely compact, light in weight, and consumes very little power according to known telecommunications receiver technology.

The attachment of the backchannel receiver module 213 to the MPX 210 permits medical personnel at a node on the network 205 (e.g., a central monitoring station 204 or similar terminal) to enter information (e.g., data or commands) on an appropriate input device, and direct the information via the backchannel transmission system 214 to the MPX 210 or the portable processor 212. Such communication may, for example, be in response to inputs or queries from attending staff that were inputted on keyboard 260. Similarly, other monitoring instruments, data processing or storage equipment, and other control and communications equipment connected to the network 205 may communicate with the backchannel receiver module 213.

As mentioned in the above, the particularly preferred embodiment of the backchannel receiver module 213 is constructed to support a communications backchannel via a paging transmission system. Most communities already employ one or more "wide-area" paging transmission systems to communicate with portable, pocket-sized receivers known as pagers. Accordingly, the backchannel receiver module 213 is constructed to take advantage of any pre-existing paging transmission system so as to provide inexpensive, two-way communication between the network 205 and the MPX 210. In particular, most hospitals already employ at least one "local-area" paging system that has been installed and dedicated for hospital use, and many hospital staff members carry a pager. Because the hospital staff members are already carrying portable processors 212 and portable computers 114 for other purposes, and will increasingly do so in the future, the benefits of the present invention are achieved without the significant expense of additional equipment and without any significant change in the way such hospitals and personnel are already operating.

Dynamic control of system configuration and patient monitoring

Further, it is a particular feature of the present invention that dynamic control may be effected of the system configuration and of the patient monitoring features and functions performed by the flexible monitoring system 200. Some of such functions may heretofore have required user intervention and/or reconfiguration of one or more of components of a conventional patient monitoring system. For the purposes of this description, dynamic control is meant to describe network-based, system-originated control of one or more of the features, functions, or tasks performed by the flexible monitoring system 200. Such features, functions, or tasks include:

Service modes, such as a remote reading of: the status of the power available to the MPX 210 or telemetry docking station 211, the signal strength of the backchannel transmitter (as received by the backchannel receiver module 213), the frequency or signal strength of the transmitter 224 in the MPX 210, or the physiological conditions currently being monitored (ECG, $SpO_2$, etc.). The service mode information may be acquired only on demand, so that the telemetry transmission bandwidth may be conserved for transmitting patient data. A particular service mode contemplated by the invention includes the transmission of new PROM code from a node on the network 205 via the backchannel transmission system 214 and the backchannel receiver module 213 for downloading into a memory device (such as an EEPROM 354 illustrated in FIG. 3).

Query the MPX Configuration, wherein a network node may query the MPX 210 for configuration data and settings, such as thresholds or other measurements (i.e. notch filter, $SpO_2$ sample rate, and frequency channel) or system information (i.e. firmware/hardware revision numbers and serial number), or to view or to edit such records as a status log. Alternatively, hospital personnel may also use the portable processor 212 to receive and answer a system-initiated query, and see the system's response.

Delivery of alarms or messages to the patient or attending staff by provision of an alarm signal (e.g. a tone) or a voice signal through a transducer on the MPX 210 or portable processor 212, or by display of textual messages on the display 258 of the portable processor 212.

Determination of the location of the MPX (and hence location of the patient) via transmission of signals from a plurality of backchannel transmission systems 214 each of which are spatially separated at fixed, known locations within the hospital, followed by measurement of the strength and delay of the signals.

Lead selection and transmitter lead fallback may be accomplished at the telemetry processor 212 before data is sent from the MPX 210. This feature also conserves the bandwidth required to transmit telemetry data, allows the MPX to transmit other parameters, or to improve forward error correction.

Redundant transmission of information, such as transmission of a waveform with 100% redundancy, thus enabling the system to compensate for dropouts in a telemetry transmission caused by multipath fading.

Dynamic power control of the radiated power level of the transmitter 224, according to the transmission path power loss. Rather than transmitting at a high enough power to overcome worst case losses, activation of this feature allows the average power consumption to be minimized, thus substantially extending battery life.

Diversity selection allows a network node to command the transmitter 224 to transmit on one of two spatially separated versions of the output element 226, e.g., either an antenna integrated in the sensor 220 and another antenna imbedded in the housing of the MPX 210.

Reuse of a selected transmission frequency by assigning a single frequency to more than one MPX 210. Such reuse is contemplated as being effected by spatial (cellular) allocation of a frequency, wherein each MPX 211 is located sufficiently distant from the others so as to overcome any channel interference. Such reuse is also contemplated as including time division multiplexing of the data transmitted from more than one MPX 211 onto one transmission channel. This feature dramatically increases the number of channels that one telemetry receiver 232 can service, and allows the flexible patient monitoring system 200 to monitor a large numbers of patients per transmission channel, and reduces errors that are caused by channel interference.

Selection of the transmission frequency (transmission channel), an otherwise costly and time consuming process, so as to change the frequency of the transmitter 224 without user intervention.

Error control according to data exchange protocols so as to correct short term dropouts (due to multipath fading). For example, the MPX 210 may send a message, then wait for a return message from the backchannel controller 214C acknowledging proper receipt. The MPX 210 may repeat the message if no acknowledgment is received.

Signal Processing and Data Transmission in the Multiport Transmitter

Figure 3:
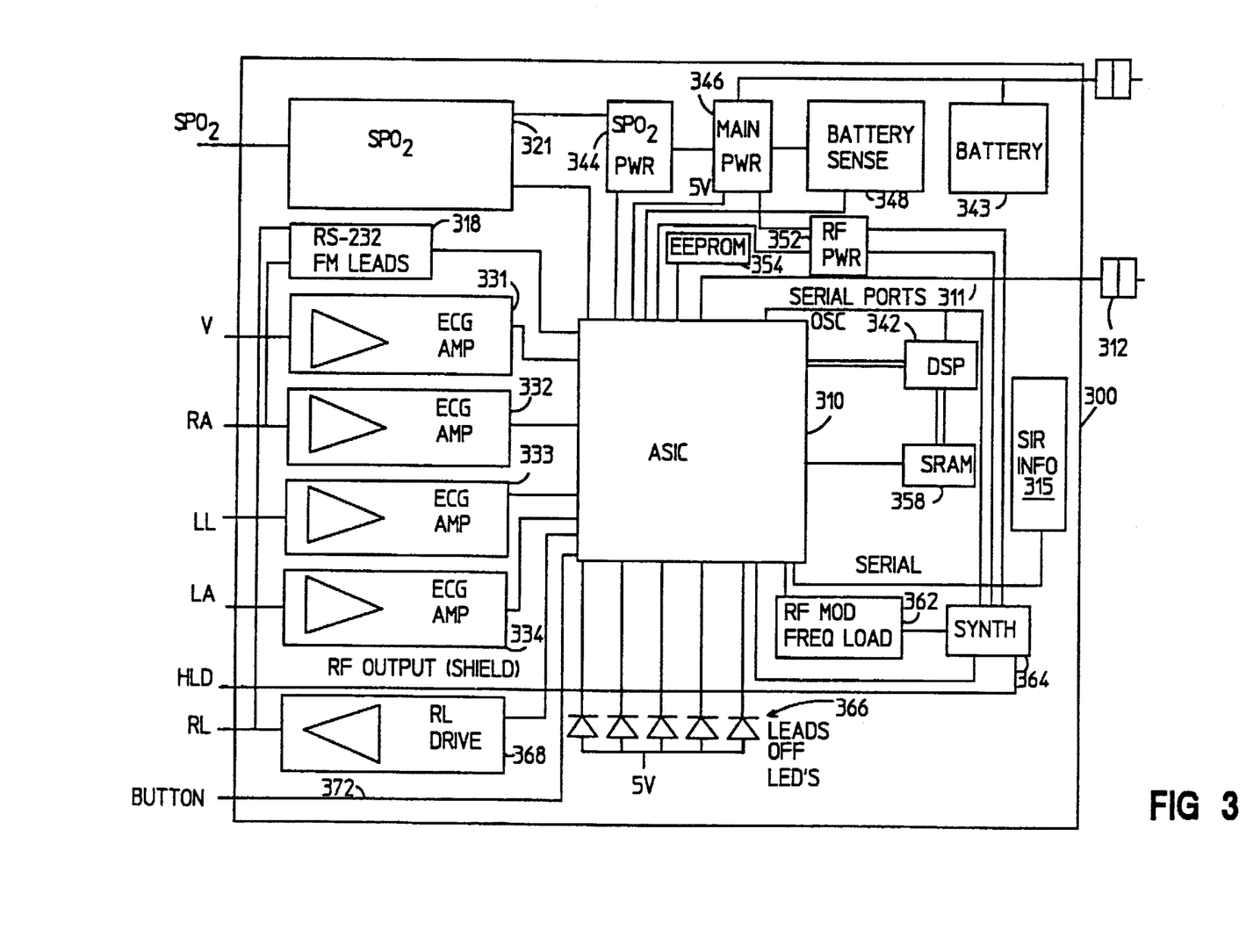
FIG. 3 is a block schematic diagram of a main portion of a multiport transmitter featured in FIGS. 1 and 2.

FIG. 3 shows an overall block diagram of a preferred embodiment of a main board 300 operable in the signal processing and data transmission section 119 of the MPX 110. The main board 300 may be considered to include five subsections: a set of ECG front ends, a $SpO_2$ monitor, an application specific integrated circuit (ASIC), a digital signal processor (DSP), and a power supply section.

The ASIC 310 is operable with at least four external signal interfaces (not including the output of transmitter 224). First and second signal interface lines 311 connect to the telemetry docking station 211; a third interface line 313 connects to a serial infrared port (SIR) 315 and the fourth interface line 314 connects to a sensor interface driver 318 (preferably in the form of a serial data port driver) which may be used to communicate to the primary monitoring instrument 201 through two leads (RA, RL) of the patient sensor (V, RA, LL, LA, RL). The ASIC 310 preferably contains universal asynchronous receiver-transmitters for performing these functions.

The serial infrared port 315 communicates using a subset of the SIR protocol. This port can be "aimed" at the portable processor 212 for establishing an unguided optical communications link, or can be attached to the fiber optic cable 244 for a more robust optical connection. Such a connection facilitates the physical coupling of the portable processor 212 and the MPX 210 for combined use during ambulatory telemetry mode.

In a particular feature of the invention, the sensor interface 318 insures patient safety by prohibiting an electrical path from a non-battery powered instrument, such as the primary monitoring instrument 201 or auxiliary monitoring instrument 202, through the MPX 210 to the patient. Also, the sensor interface 318 will sense a voltage on one of the conductors in the connection to the primary monitoring instrument 201; the ASIC 310 will only connect a serial data driver to the patient leads when it senses this voltage. This insures that there is no harm to the patient by inadvertent application of serial data to the sensor, which may be already connected to the patient.

An $SpO_2$ monitoring section 321 produces data representative of the arterial oxygen saturation value, the pulse rate, and relative perfusion. The $SpO_2$ monitoring section 321 will connect directly to an appropriate $SpO_2$ sensor (not shown) such as may be obtained from Hewlett-Packard Company, Nellcor, or Ohmeda.

Additional circuitry connected to the ASIC 310 include: four ECG front ends 331, 332, 333, 334; a battery 343; a $SpO_2$ monitor power supply circuit 344; a main power supply circuit 346; a battery sense circuit 348; a transmitter power supply circuit 352; a programmable memory storage device preferably in the form of an electrically-erasable programmable read-only memory (EEPROM) chip 354; a digital signal processor (DSP) chip 342; a static memory storage device, preferably in the form of a static random access memory (SRAM) 358; a radio-frequency (RF) modulator 362; and a radio frequency synthesizer 364. Also connected to the ASIC 310 are a set of leads-off indicators, each preferably in the form of a light-emitting diode (LED) array 366, and a RL lead driver circuit 368. The ASIC 310 handles the task of interfacing to the ECG hardware, the nurse call button, the leads off indicators; and the ASIC 310 controls signals to and from the SpO$_2$ circuit 321, the primary monitoring instrument 201, the SIR port 315, and the two serial port lines 311.

The EEPROM 354 preferably contains frequency, patient identification, and system configuration information. By performing all data processing tasks in the DSP 356, which is set to by direct boot from the EEPROM 354, future software upgrades are made easily through the serial port lines 311.

Additional main board hardware architecture includes:

Nurse Call Button: A signal on a nurse call button line 372 may be configured to cause the ASIC 310 to run a recording, set off the nurse call alarm, or perform another communication function such as what is known as spoof coding, which may be used by a technician to match a MPX 210 to a telemetry receiver 232.

Power Supply Control: Control lines from the ASIC 310 may be operated to selectively shut down certain power subsections, as will be described below.

Internal Power Source: Preferably, a battery 343 is a Alkaline, Zinc-Air, or Carbon-Zinc 8.4 or 9 volt battery for use when the MPX 210 is not configured to monitor SpO$_2$; when SpO$_2$ is used, a lithium battery is preferred.

Visual indicators: Five indicators preferably in the form of light emitting diodes 366 are situated on the exterior of the MPX 210 with each indicator located under the respective electrode that corresponds to a lead. The DSP 342 activates an appropriate indicator after a change of state (e.g., leads-off condition) in any lead wire. Also, some or all of the LEDs may be activated in a predetermined pattern to indicate that the MPX fails a self-test, or to indicate the signal strength received by the SIR 315.

Power Supply: The main power supply section 346 is a linear or switch mode power supply that converts power from the battery 343 for provision to the SpO$_2$ power supply subsection 344, transmitter power supply subsection 352, and battery sense subsection 348. Additionally, the MPX 210 may source power from the telemetry docking station 211 or the sensor 220 via diodes that are connected to the main power supply section 346. For example, when the primary monitoring instrument 201 is employed in instrument telemetry mode and power from the battery 343 is to be conserved, the presence of a minimum of 9V on the shield of the RL lead causes the main power supply 346 to draw its power from the sensor 220. Patient isolation is achieved by preventing simultaneous connections to both the patient and to power from the primary monitoring instrument 201.

Battery Sense Section: The battery sense section 348, under control of the ASIC 310, effects control of all of the power supply subsections. For example, the SpO$_2$ monitoring, transmitter, ECG monitoring, or communications functions may be individually shut down by the ASIC 310 to conserve power. The ASIC 310 also provides, based on signals from the battery sense section, advance warning messages that are displayed on the network 205 or the display 258, such as "replace battery" or "weak battery".

Backchannel Receiver Module

Figure 4:
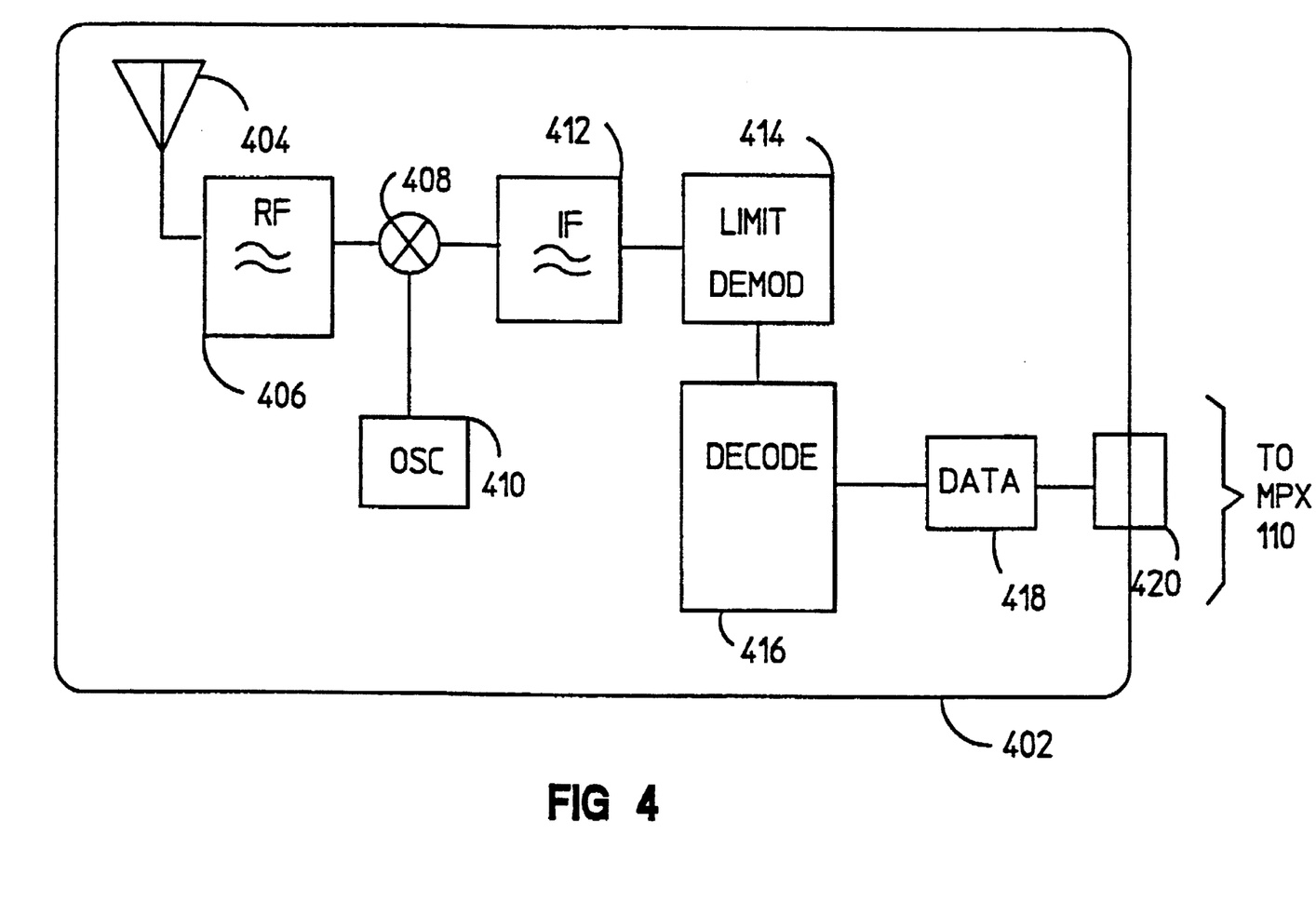
FIG. 4 is a block schematic diagram of a backchannel receiver module featured in FIGS. 1 and 2.

FIG. 4 illustrates a particularly preferred embodiment 402 of the backchannel receiver module 213 of FIG. 2. The paging backchannel receiver module 402 preferably receives frequency-modulated (FM) transmissions at certain paging transmission frequencies, which currently include frequencies in the range of 30–50 megahertz (mHz), 150–174 mHz, 450–512 mHz, or 800–1000 mHz. These transmissions are received by an antenna 404 that is preferably integrally mounted on the backchannel receiver module 402, and filtered by a RF filter stage 406 before being passed to a mixer 408. The output of an oscillator 410 mixed with the filtered RF signal is output to an intermediate frequency (IF) filter stage 412. The IF filtered signal is then passed to a limiter/demodulator stage 414 and a decoding stage 416. The decoded signal output is provided to a data transfer stage 418 for transfer through a data and power connector 420 to the MPX 110.

Telemetry Docking Station—Detailed Architecture

Figure 5:
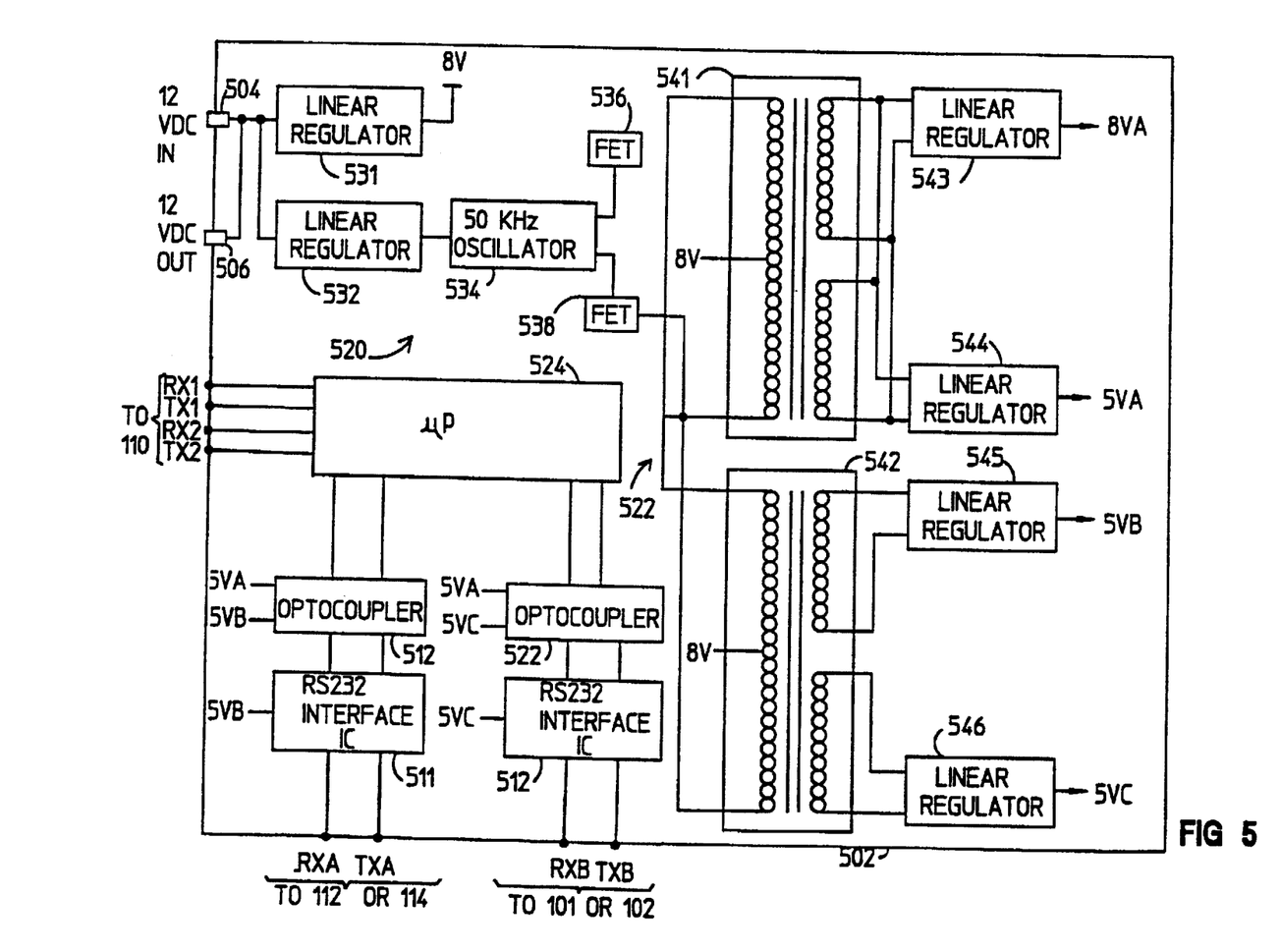
FIG. 5 is block schematic diagram of a telemetry docking station featured in FIGS. 1 and 2.

With reference to FIG. 5, a preferred embodiment of the data and power handling circuitry 502 of the telemetry docking station 211 will be understood to include: a) first and second data communication interface sections 511, 512 to enable the MPX 210 to interface with data paths from external devices (preferably, devices such as the portable processor 212 and one or more monitoring instruments, such as the primary monitoring instrument 201 and an auxiliary monitoring instrument 202); b) a power conversion section 520 and a power transformer section 522 to enable units such as the MPX 210 or portable processor 212 to receive isolated, regulated power from external power sources; and c) a data processing section 524 preferably in the form of a microprocessor for performing data protocol translation and other data interfacing functions. The telemetry docking station 211 preferably incorporates microminiature components and circuitry so as to provide the aforementioned functions in a compact, portable Unit that is positionable adjacent, or attachable to, the portable processor 212 and/or the portable computer 114.

A DC input power jack 504 preferably receives 12VDC from a conventional AC-to-DC wall outlet converter, certified as an IEC-601-1 medically approved device, such as are commercially available for powering portable medical electronic devices. A DC out jack 506 provides 12VDC to the portable processor 212. A first serial interface circuit 511 and a second serial interface circuit 512 have respective connections RXA, TXA and RXB, TXB. The first and second interface circuits 511, 512 are also respectively coupled to the MPX 210 via optocouplers 521, 522 and connections RX2, TX2, RX1, and TX1.

The received 12VDC power from the charger is passed through first and second linear regulators 531, 532; the regulated power is further passed to an oscillator 534 and to first and second field-effect transistor (FET) stages 536, 538 before being fed to the primary sides of first and second transformers 541, 542. Linear regulators 543, 544, 545, 546 regulate the output of the transformers 541, 542. Additional protection circuitry (not shown) may include a fuse or a breaker may be included to prevent excessive DC current flow in the event of a FET or oscillator failure, and transient suppression circuitry to suppress power surges and transients in the incoming DC line. Some of the voltages thus produced are:

8V—transformer primaries

5V—power to oscillator 534

8VA—isolated power to the MPX 210

5VA—isolated power to local side of optocouplers 521, 522

5VB—Isolated power to remote side of optocoupler 521

5VC—Isolated power to remote side of optocoupler 522

This illustrated circuit uses the transformers 541, 542 to provide at least 6 kV isolation to effect a barrier between the patient 218 and non-battery power sources. The telemetry docking station 211 thus provides these features:

a. power line isolation by the use of an IEC-601-1 medically-approved wall charger;

b. patient isolation by use of isolated power supplies;

c. serial data optical isolation;

d. defibrillation isolation, by employing recessed pins in all external connectors on the MPX 210.

While the invention has been particularly shown and described above with reference to preferred embodiments, changes in form and detail may be made by one skilled in the art to the foregoing embodiments without departing from the spirit and scope of the invention.

What is claimed is:

1. A flexible patient monitoring system for use in monitoring a selected plurality of physiological conditions of a patient in a medical care environment, comprising:

a multiport transmitter including as integral components therein:

a sensor system for providing a sense signal representative of the selected plurality of physiological conditions;

a monitoring section connected to the sensor system for receiving the sense signal and providing sense data representative of the plurality of physiological conditions, a first data port for receiving first data and a second data port for receiving second data;

a data processing and signal transmission section operatively connected to the monitoring section and first and second data ports for processing the sense data and the first and second data so as to provide processed data, and for transmitting the processed data as a telemetry signal; and a housing for integrating said sensor system, monitoring section, first and second data ports, and data processing and signal transmission section in a portable unit, said multiport transmitter thereby being optionally borne by the patient while said plurality of physiological conditions are monitored.

2. The flexible patient monitoring system of claim 1, further comprising a monitoring instrument, wherein the first data port includes means for connecting at least a selected one of said first and second data ports to the monitoring instrument for thereby receiving said first data from the monitoring instrument, said multiport transmitter thereby being optionally connectable to the monitoring instrument while said plurality of physiological conditions are monitored.

3. The flexible patient monitoring system of claim 1, further comprising a monitoring instrument, wherein the sensor system includes means for connecting the sensor system to the monitoring instrument for thereby receiving a selected one of said first and second data from the monitoring instrument, said multiport transmitter thereby being optionally connectable to the monitoring instrument while said plurality of physiological conditions are monitored.

4. The flexible patient monitoring system of claim 1, wherein the data processing and signal transmission section include means for outputting the processed data from at least a selected one of said first and second data ports, and further comprising a telemetry subsystem interface having a data input device, a data output device, an interface data input/output section, a docking station data port associated with said data input/output section, and a processor, wherein the selected one of first and second data ports includes means for connecting the multiport transmitter with a selected one of the data input device and the data output device on the telemetry subsystem interface for transfer of the processed data therebetween, and wherein the processor includes means for selectably outputting the processed data to the data output device.

5. The flexible patient monitoring system of claim 4, wherein the selected one of the data input device and the data output device, and the means for connecting the multiport transmitter with a selected one of the data input device and the data output device each further comprise an optical transceiver for transferring the processed data therebetween on a modulated light beam.

6. The flexible patient monitoring system of claim 4, wherein the telemetry subsystem interface further comprises a portable computer.

7. The flexible patient monitoring system of claim 6, wherein the portable computer further comprises a palmtop computer.

8. The flexible patient monitoring system of claim 1, wherein the data processing and signal transmission section include means for outputting said processed data from at least a selected one of said first and second data ports, and further comprising a telemetry docking station having data transfer means for connecting the telemetry docking station to the selected one of said first and second data ports for transferring at least a selected one of said first data, second data, and said processed data between said multiport transmitter and said telemetry docking station.

9. The flexible patient monitoring system of claim 8, wherein the multiport transmitter further comprises a power port for receiving operating power and supplying such operating power to at least one of said sensor system, monitoring section, and data processing and signal transmission section, and wherein the telemetry docking station further comprises:

a power section for receiving externally-sourced power;

an isolation section connected to the power section and having a power converter for converting the externally-sourced power to isolated power; and a second power port connected to the isolation section and being connectable to the power port for transferring isolated operating power therebetween.

10. The flexible patient monitoring system of claim 9, wherein the isolation section further comprises means for transferring at least one of said first data, second data, and said processed data between the multiport transmitter and the telemetry docking station, and wherein the isolation section further comprises a data isolator for receiving and isolating the data thus transferred.

11. The flexible patient monitoring system of claim 10, further comprising a monitoring instrument, and wherein the data transfer means includes means for transferring at least one of said first data, second data, and said processed data between the multiport transmitter and the monitoring instrument.

12. The flexible patient monitoring system of claim 10, further comprising a telemetry subsystem interface, and wherein the data transfer means includes means for transferring at least one of said first data, second data, and said processed data between the multiport transmitter and the telemetry subsystem interface.

13. The flexible patient monitoring system of claim 10, further comprising a telemetry subsystem interface, and wherein the data transfer means includes means for connecting the telemetry docking station to the telemetry subsystem interface for transferring at least one of said first data, second data, and said processed data between said multiport transmitter and said telemetry subsystem interface.

14. The flexible patient monitoring system of claim 8, further comprising:

a telemetry receiving system for receiving and processing the telemetry signal so as to provide telemetry information;

a network controller operatively connected to the telemetry receiving system for providing networked telemetry information from said telemetry information; and a communications network having an information access device, a first node, and a second node, said first node being connected to the network controller for receiving the networked telemetry information and said information access device being connected to the second node for accessing the networked telemetry information.

15. The flexible patient monitoring system of claim 14, wherein the flexible patient monitoring system may be configured to operate in at least one of four modes: ambulatory telemetry mode, wherein the multiport transmitter is operated independently of the monitoring instrument and the telemetry docking station; docked telemetry mode, wherein the multiport transmitter is connected to the telemetry docking station for transfer of data and power between the multiport transmitter and the docking station; simple instrument telemetry mode, wherein the multiport transmitter and the monitoring instrument are connected together for transfer therebetween of said selected one of said first, second, and processed data; and docked instrument telemetry mode, wherein the multiport transmitter and the monitoring instrument are connected to the telemetry docking station for transfer of said selected one of said first, second, and processed data between the multiport transmitter, the telemetry docking station, and the monitoring instrument.

16. A multiport transmitter for use in a flexible patient monitoring system for monitoring a selected plurality of physiological conditions of a patient in a medical care environment, the system including a first monitoring instrument for monitoring at least one of said selected plurality of physiological parameters and providing a respective first instrument signal, comprising as integral components therein:

a sensor including means for connecting the multiport transmitter in a first mode to the monitoring instrument for acquiring an instrument signal, and means for connecting the multiport transmitter in a second mode to the patient for acquiring a patient parameter signal;

a sensor interface connected to the sensor and operable in the first mode for selecting the instrument signal from the sensor and in a second mode for selecting the patient parameter signal from the sensor, and in response providing a selected monitor signal;

a processing section connected to the sensor interface for processing the selected monitor signal and for providing, in response to said processing, processed data;

a data output port connected to the processing section for outputting the processed data; and a radio frequency transmitter connected to the data output port for transmitting the processed data as a telemetry signal.

17. The multiport transmitter of claim 16, wherein the flexible patient monitoring system includes a second monitoring instrument, and wherein the multiport transmitter further comprises a second monitoring instrument data input port connected to the sensor interface for receiving a second instrument signal from the second monitoring instrument, and wherein the sensor interface is operable in a third mode for selecting the second instrument signal, and in response providing the second instrument signal as the selected monitor signal.

* * * * *